(12) United States Patent
Huang

(10) Patent No.: US 8,666,140 B2
(45) Date of Patent: Mar. 4, 2014

(54) DEFECT INSPECTION METHOD FOR WAFER AND WAFER DEFECT INSPECTION SYSTEM USING THE SAME

(75) Inventor: Kai-Ping Huang, Eastvale (SG)

(73) Assignee: United Microelectronics Corp., Hsinchu (TW)

( * ) Notice: Subject to any disclaimer, the term of this patent is extended or adjusted under 35 U.S.C. 154(b) by 35 days.

(21) Appl. No.: 13/352,432

(22) Filed: Jan. 18, 2012

(65) Prior Publication Data

US 2013/0182938 A1 Jul. 18, 2013

(51) Int. Cl.
*G06K 9/00* (2006.01)

(52) U.S. Cl.
USPC .......................................... 382/149

(58) Field of Classification Search
None
See application file for complete search history.

(56) References Cited

U.S. PATENT DOCUMENTS

| | | | |
|---|---|---|---|
| 2002/0130262 A1* | 9/2002 | Nakasuji et al. | 250/311 |
| 2003/0200523 A1* | 10/2003 | Takahashi et al. | 716/19 |
| 2004/0228515 A1* | 11/2004 | Okabe et al. | 382/145 |
| 2005/0004774 A1* | 1/2005 | Volk et al. | 702/108 |
| 2005/0255611 A1* | 11/2005 | Patterson et al. | 438/14 |
| 2007/0035728 A1* | 2/2007 | Kekare et al. | 356/237.5 |
| 2007/0201018 A1* | 8/2007 | Takeda et al. | 356/237.2 |
| 2008/0240544 A1 | 10/2008 | Sato | |
| 2008/0254701 A1* | 10/2008 | Koshiishi et al. | 445/2 |
| 2011/0308846 A1* | 12/2011 | Ichiki | 174/257 |

* cited by examiner

*Primary Examiner* — Stephen R Koziol
*Assistant Examiner* — Delomia Gilliard
(74) *Attorney, Agent, or Firm* — Ding Yu Tan

(57) ABSTRACT

A defect inspection method for a wafer is provided. The wafer comprises a component pattern. The method comprises the following steps: providing a defect inspection apparatus for inspecting the defects on the wafer to obtain a defect distribution map; providing a photo mask, wherein the photo mask comprises a exposure pattern corresponding to the component pattern; and comparing the defect distribution map with the exposure pattern and dividing the defects in the defect distribution map into a first killer defect group and a first non-killer defect group according to their corresponding locations in the exposure pattern. In addition, a wafer defect inspection system applying the same method is also provided.

12 Claims, 5 Drawing Sheets

US 8,666,140 B2

DEFECT INSPECTION METHOD FOR WAFER AND WAFER DEFECT INSPECTION SYSTEM USING THE SAME

FIELD OF THE INVENTION

The present invention relates to wafer defect inspection, and particularly relates to a defect inspection method for a wafer and a wafer defect inspection system using the method.

BACKGROUND OF THE INVENTION

With size of the components of the integrated circuits increasingly narrowed, the defects produced in process are very easy to cause problems of product yield drop. For the present, a conventional defect inspection method is using an inspection device to perform inline automatic defect classification to obtain a defect distribution map, and then the defect distribution map is analyzed by experienced engineers.

In the use of the inspection device, users need to set up the information of the various types of known killer defects in advance, so that the inspection device is able to determine known killer defects in accordance with the aforementioned information. However, the inspection device cannot determine the defects of unknown types. Therefore, the conventional defect inspection method lacks of efficiency and is not accurate enough.

SUMMARY OF THE INVENTION

One embodiment relates to a defect inspection method for a wafer. The wafer comprises a first component pattern formed thereon. The method comprises the following steps: providing a defect inspection apparatus for inspecting the defects on the wafer and obtaining a defect distribution map; providing a first photo mask, wherein the first photo mask comprises a first exposure pattern corresponding to the first component pattern; and comparing the defect distribution map with the first exposure pattern and dividing the defects in the defect distribution map into a first killer defect group and a first non-killer defect group according to their corresponding locations in the first exposure pattern.

Another embodiment relates to a wafer defect inspection system. The system comprises a defect inspection apparatus and a comparing device. The defect inspection apparatus is configured for inspecting defects on a wafer with a first component pattern formed thereon and obtaining a defect distribution map. The comparing device is configured for receiving the defect distribution map and acquiring a first exposure pattern corresponding to the first component pattern on a first photo mask, so as to compare the defect distribution map with the first exposure pattern and divide the defects in the defect distribution map into a first killer defect group and a first non-killer defect group according to their corresponding locations in the first exposure pattern.

The method to solve the problems of the present invention is to use a wafer defect inspection system to inspect defects on a wafer with a component pattern formed thereon and obtain a defect distribution map. After the defect distribution map has been obtained, the defect distribution map is compared with the first exposure pattern, and the defects in the defect distribution map are divided into a first killer defect group and a first non-killer defect group according to their corresponding locations in the first exposure pattern. Engineers only need to perform a defect analysis on the defects in the first killer defect group, greatly enhancing the efficiency of the engineers and promoting the accuracy of the inspection.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
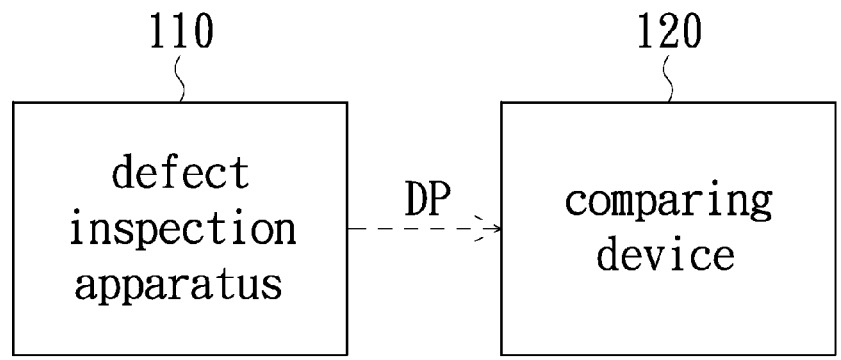
FIG. 1 is a schematic view of a wafer defect inspection system in an embodiment of present invention.

FIG. 1 is a schematic view of a wafer defect inspection system in an embodiment of present invention. In the present invention, a wafer is a general base material or a substrate. In accordance with different materials, the wafer can be a silicon wafer, a glass wafer, a silicon-on-insulator (SOI) wafer and so on, and it has no shape or size restrictions.

Figure 2:
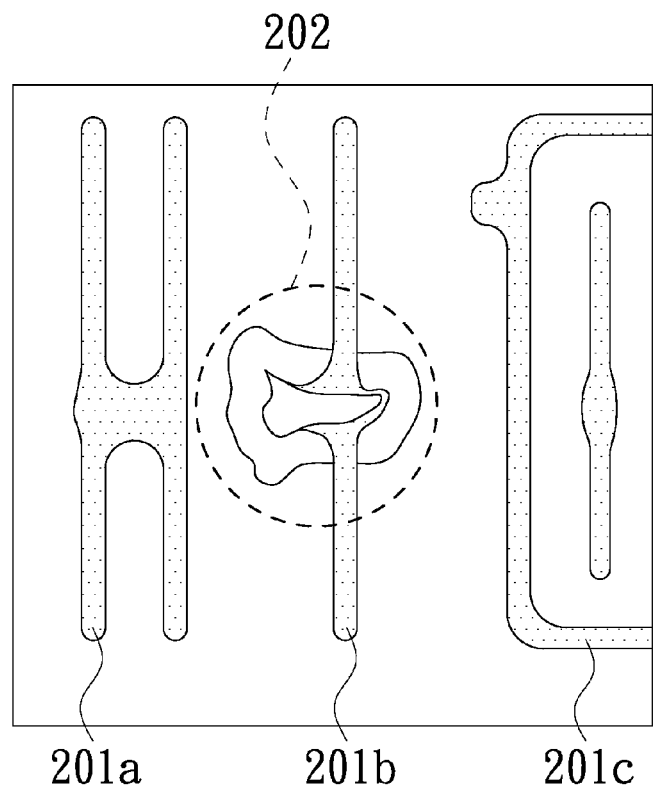
FIG. 2 is a partially enlarged view of a wafer with a first component pattern.
Figure 3:
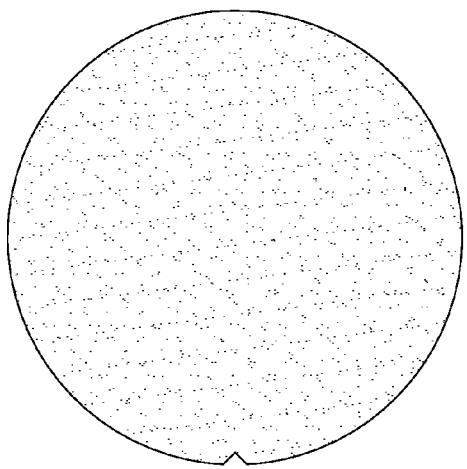
FIG. 3 is a schematic view of a defect distribution map.
Figure 4:
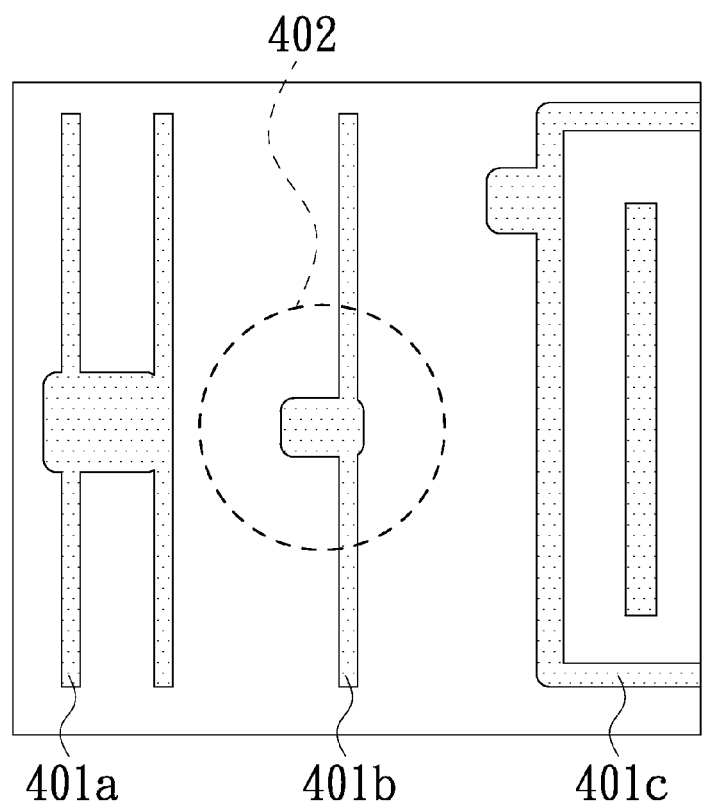
FIG. 4 is a partially enlarged view of a first exposure pattern of a first photo mask.

Referring to FIG. 1, the wafer defect inspection system 10 comprises a defect inspection apparatus 110 and a comparing device 120. The defect inspection apparatus 110 is configured for inspecting defects on a wafer with a first component pattern formed thereon and obtaining a defect distribution map DP. FIG. 2 is a partially enlarged view of a wafer with a first component pattern. In FIG. 2, 201a~201c labeled as a part of the first component pattern on the wafer, and 202 labeled as a defect. FIG. 3 is a schematic view of a defect distribution map. Black spots in FIG. 3 show the locations of the defects on the wafer. Referring to FIG. 1 again, the comparing device 120 is configured for receiving the defect distribution map DP and acquiring a first exposure pattern corresponding to the first component pattern on a first photo mask. FIG. 4 is a partially enlarged view of a first exposure pattern of the first photo mask. In FIG. 4, 401a~401c labeled as parts of the first exposure pattern corresponding to the first component pattern 201a~201c.

Figure 6:
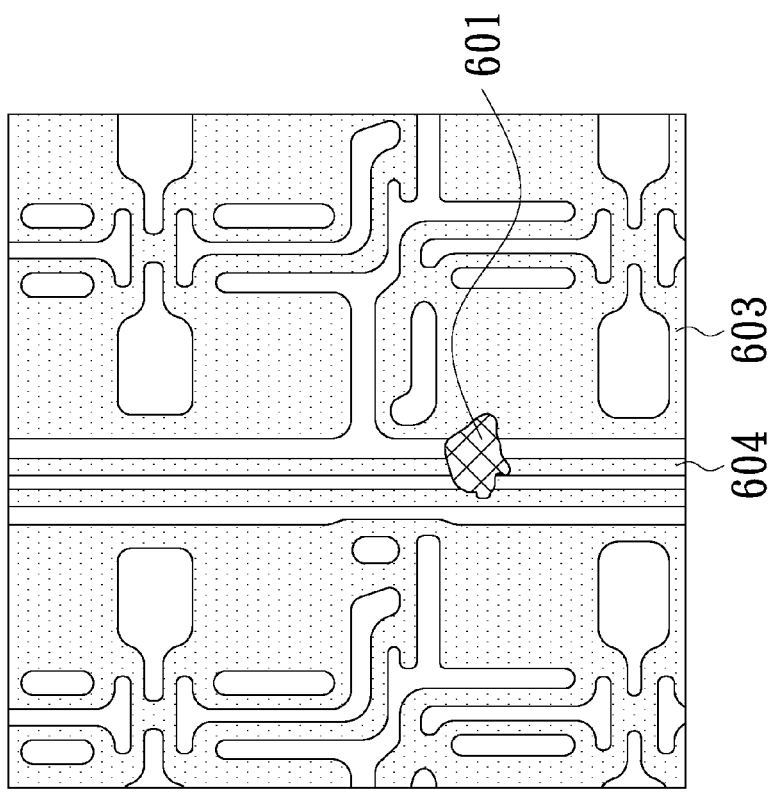
FIG. 6 is a partially enlarged view of a wafer with a first component pattern.
Figure 5:
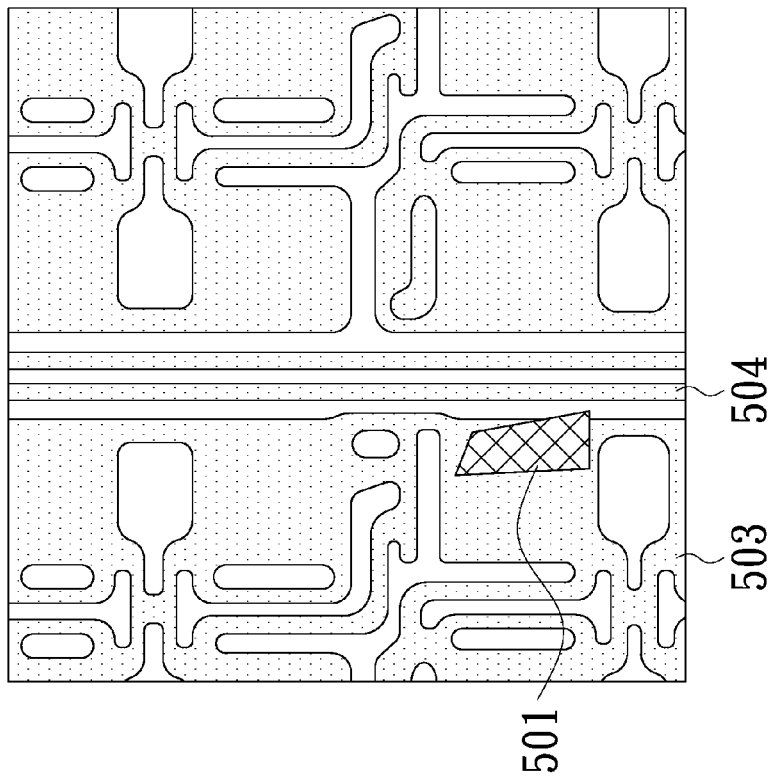
FIG. 5 is a partially enlarged view of a wafer with a first component pattern.

Referring to FIG. 1 again, after receiving the first exposure pattern, the comparing device 120 compares the defect distribution map DP with the first exposure pattern and divides the defects in the defect distribution map DP with the first exposure pattern and divides the defects in the defect distribution map into a first killer defect group and a first non-killer defect group according to their corresponding locations in the first exposure pattern. Referring to FIGS. 2 and 4, depending on the corresponding location 402 of the defect 202 on the first exposure pattern, the defect 202 will not cause an open circuit or a short circuit, so the defect 202 belongs to the first non-killer defect group. In contrast, if the defect 202 will cause an open circuit or a short circuit, the defect 202 belongs to the first killer defect group. FIG. 5 and FIG. 6 show the difference between the killer defect and the non-killer defect. FIG. 5 and FIG. 6 both are partially enlarged views of a wafer with a first component pattern. Referring to FIG. 5, depending on the corresponding location of the defect 501, the conductive part 503 and the conductive part 504 will not be electrically connected with each other by the defect 501, so the defect 501 belongs to the first non-killer defect group. Referring to FIG. 6, depending on the corresponding location of the defect 601, the conductive part 603 and the conductive part 604 will be electrically connected with each other by the defect 601, so the defect 601 belongs to the first killer defect group.

Figure 7:
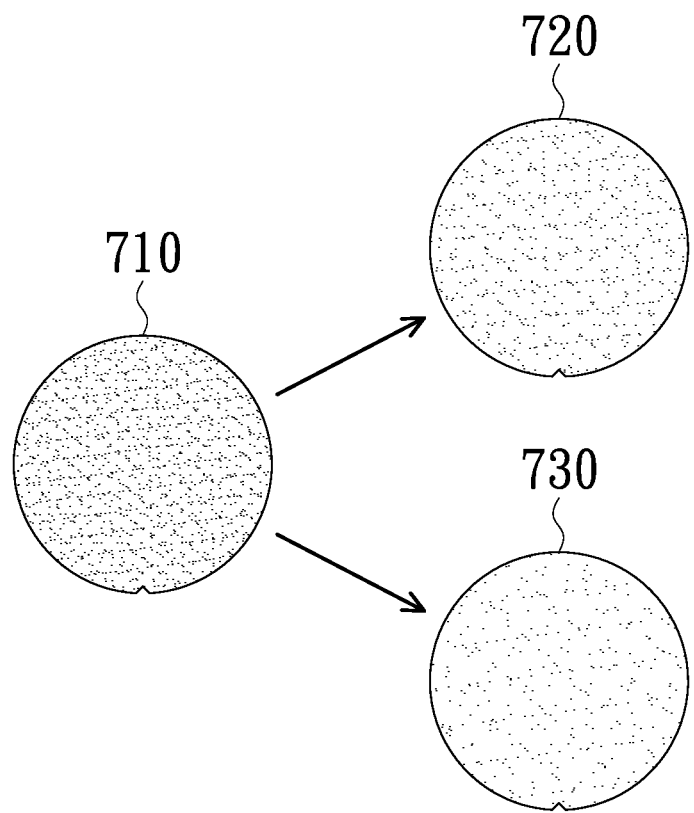
FIG. 7 is a schematic view of defects in the defect distribution map divided into a first killer defect group and a first non-killer defect.

From the foregoing, a method for the comparing device 120 to determine whether a defect will cause a short circuit comprises the following sub-steps: determining the corresponding location of the defect in the first exposure pattern, and determining whether two different conductive parts shown in the first exposure pattern will be electrically connected with each other by the defect if the defect is at the corresponding location. Accordance with the above method, the comparing device 120 can determine whether a defect in the defect distribution map belongs to the first killer defect group or not, just like what FIG. 7 shows. FIG. 7 is a schematic view of defects in the defect distribution map divided into a first killer defect group and a first non-killer defect. In FIG. 7, 710 labeled as the defect distribution map, 720 labeled as the defect distribution map only has the first killer defect group, and 730 labeled as the defect distribution map only has the first non-killer defect group.

In addition, the first exposure pattern in the present invention can be divided into at least one critical pattern area and at least one non-critical pattern area in accordance with density, shape, or texture thereof. The so-called critical pattern area, for example, is an area in which different conductive parts are so close that any two conductive parts are easily to be electrically connected with each other by a defect appeared therein. The so-called non-critical pattern area, for example, is an area in which different conductive parts are so loose that any two conductive parts are hard to be electrically connected with each other by a defect appeared therein. That is, the defects located in the critical pattern area can be regarded as killer defects, and the defects located in the non-critical pattern area can be regarded as non-killer defects.

By the above description, it can be seen that after all of the defects in the defect distribution map have been divided into a first killer defect group and a first non-killer defect group, engineers only need to perform a defect analysis on the defects in the first killer defect group, greatly enhancing the efficiency of the engineers.

In addition, as an integrated circuit device typically has several routing layers, the wafer mentioned above may further comprises a second component pattern, and the second component pattern and the first component pattern belong to two different routing layers. In order to determine whether a defect in the defect distribution map will affect the other routing layer, the comparing device 120 is further configured for acquiring a second exposure pattern, so as to compare the defect distribution map with the second exposure pattern and divide the defects in the defect distribution map into a second killer defect group and a second non-killer defect group according to their corresponding locations in the second exposure pattern. The second exposure pattern corresponds to the second component patter formed on a second photo mask.

Certainly, the second exposure pattern can also be divided into at least one second critical pattern area and at least one second non-critical pattern area. The comparing device 120 can also divide the defects in the second critical pattern area of the second exposure pattern into the second killer defect group and divide the defects in the second non-critical pattern area of the second exposure pattern into the second non-killer defect group.

Figure 8:
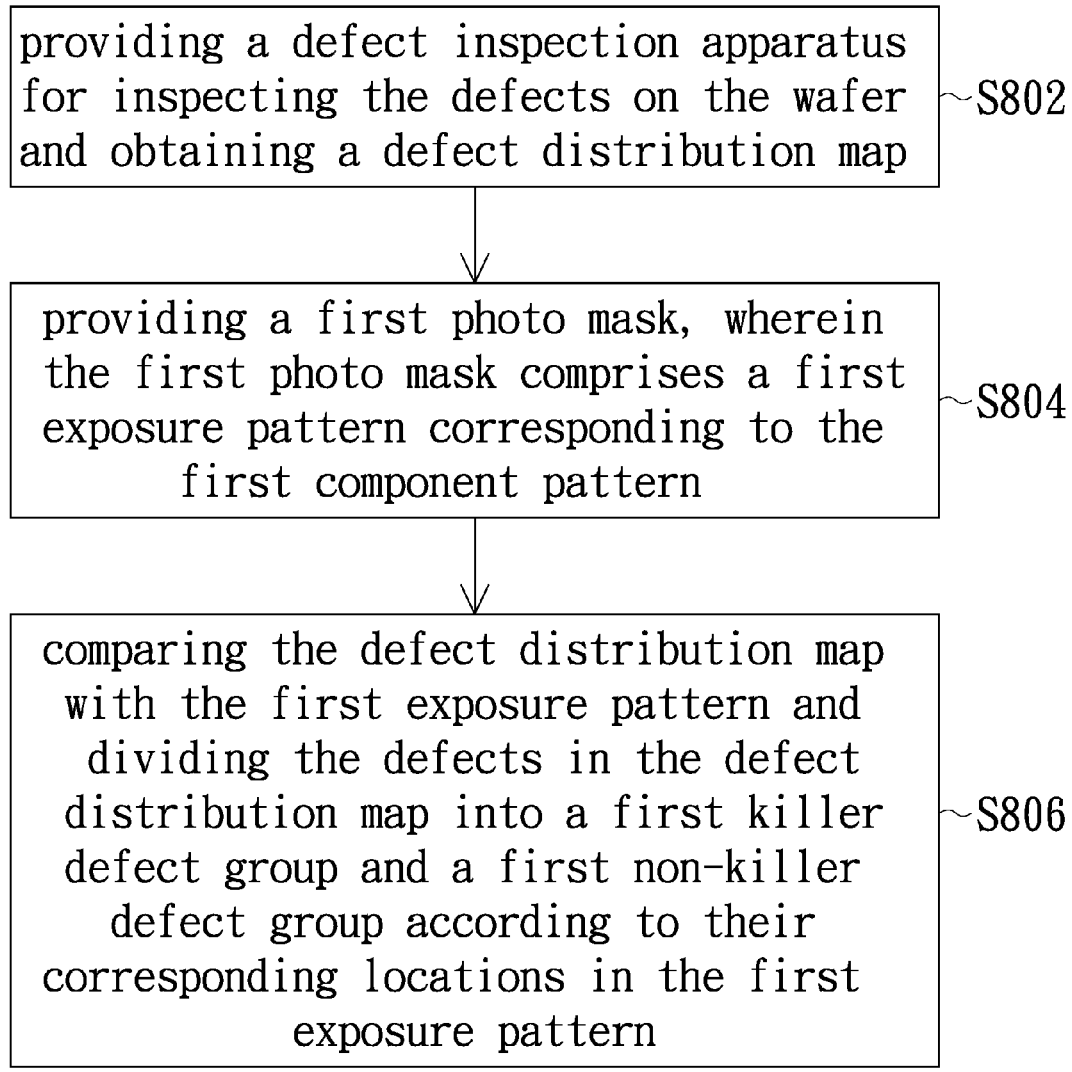
FIG. 8 is a flow chart of a defect inspection method for a wafer in an embodiment of present invention.

Steps of a defect inspection method can be summed up by the above examples. FIG. 8 is a flow chart of a defect inspection method for a wafer of present invention. The wafer comprises a component pattern. Referring to FIG. 8, the defect inspection method comprises the following steps. Firstly, a defect inspection apparatus is provided and adapted to inspect the defects on the wafer to obtain a defect distribution map (see step S802). Then, a photo mask with a first exposure pattern is provided, and the first exposure pattern corresponds to the first component pattern (see step S804). And then, the defect distribution map is compared with the first exposure pattern, and the defects in the defect distribution map are divided into a first killer defect group and a first non-killer defect group according to their corresponding locations in the first exposure pattern (see step S806).

In summary, the present invention provides a wafer defect inspection system to inspect defects on a wafer with a component pattern formed thereon and obtain a defect distribution map. After the defect distribution map has been obtained, the defect distribution map is compared with the first exposure pattern, and the defects in the defect distribution map are divided into a first killer defect group and a first non-killer defect group according to their corresponding locations in the first exposure pattern. Engineers only need to perform a defect analysis on the defects in the first killer defect group, greatly enhancing the efficiency of the engineers and promoting the accuracy of the inspection.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A defect inspection method for a wafer, the wafer including a first component pattern formed thereon, the method comprising the following steps:
    providing a defect inspection apparatus for inspecting the defects on the wafer and obtaining a defect map;
    providing a first photo mask, wherein the first photo mask comprises a first exposure pattern corresponding to the first component pattern; and
    comparing the defect map with the first exposure pattern and dividing the defects in the defect map into a first killer defect group and a first non-killer defect group, wherein the first killer defect group comprises more than one defect, and the first killer defect group is divided according to the defects' corresponding locations in the first exposure pattern, the first non-killer defect group comprises more than one defect, and the first non-killer defect group is divided according to the defects' corresponding locations in the first exposure pattern.

2. The method of claim 1, wherein each defect in the first killer defect group will cause an open circuit or a short circuit, and each defect in the first non-killer defect group will not cause an open circuit or a short circuit.

3. The method of claim 2, wherein the step of determining whether a defect will cause a short circuit comprises the following sub-steps:
   determining the corresponding location of the defect in the first exposure pattern; and
   determining whether two different conductive parts showed in the first exposure pattern will be electrically connected with each other by the defect if the defect is at the corresponding location.

4. The method of claim 1, wherein the first exposure pattern comprises a first critical pattern area and a first non-critical pattern area, and the defect inspection method further comprises the following steps:
   dividing the defects in the first critical pattern area into the first killer defect group; and
   dividing the defects in the first non-critical pattern area into the first non-killer defect group.

5. The method of claim 1, wherein the wafer further comprises a second component pattern, the second component pattern and the first component pattern belong to two different routing layers, and the defect inspection method further comprises the following steps:
   proving a second photo mask, the second photo mask comprising a second exposure pattern corresponding to the second component pattern; and
   comparing the defect map with the second exposure pattern and dividing the defects in the defect map into a second killer defect group and a second non-killer defect group according to their corresponding locations in the second exposure pattern.

6. The method of claim 5, wherein the second exposure pattern comprises a second critical pattern area and a second non-critical pattern area, and the defect inspection method further comprises the following steps:
   dividing the defects in the second critical pattern area into the second killer defect group; and
   dividing the defects in the second non-critical pattern area into the second non-killer defect group.

7. A wafer defect inspection system, comprising:
   a defect inspection apparatus for inspecting defects on a wafer with a first component pattern formed thereon and obtaining a defect map; and
   a comparing device for receiving the defect map and acquiring a first exposure pattern corresponding to the first component pattern on a first photo mask, so as to compare the defect map with the first exposure pattern and divide the defects in the defect map into a first killer defect group and a first non-killer defect group, wherein the first killer defect group comprises more than one defect, and the first killer defect group is divided according to the defects' corresponding locations in the first exposure pattern, the first non-killer defect group comprises more than one defect, and the first non-killer defect group is divided according to the defects' corresponding locations in the first exposure pattern.

8. The system of claim 7, wherein each defect in the first killer defect group will cause an open circuit or a short circuit, and each defect in the first non-killer defect group will not cause an open circuit or a short circuit.

9. The system of claim 8, wherein the comparing device determines whether a defect will cause a short circuit by the following sub-steps:
   determining the corresponding location of the defect in the first exposure pattern; and
   determining whether two different conductive parts showed in the first exposure pattern will be electrically connected with each other by the defect if the defect is at the corresponding location.

10. The system of claim 7, wherein the first exposure pattern comprises a first critical pattern area and a first non-critical pattern area, and the comparing device is used for dividing the defects in the first critical pattern area into the first killer defect group and dividing the defects in the first non-critical pattern area into the first non-killer defect group.

11. The system of claim 7, wherein the wafer further comprises a second component pattern, the second component pattern and the first component pattern belong to two different routing layers, and the comparing device is further configured for acquiring a second exposure pattern corresponding to the second component pattern on a second photo mask, so as to compare the defect map with the second exposure pattern and divide the defects in the defect map into a second killer defect group and a second non-killer defect group according to their corresponding locations in the second exposure pattern.

12. The system of claim 11, wherein the second exposure pattern comprises a second critical pattern area and a second non-critical pattern area, and the comparing device is used for dividing the defects in the second critical pattern area into the second killer defect group and dividing the defects in the second non-critical pattern area into the second non-killer defect group.

* * * * *